United States Patent
Salick Ryan et al.

(10) Patent No.: US 9,248,194 B2
(45) Date of Patent: Feb. 2, 2016

(54) AFFINITY PEPTIDES TOWARD INFLIXIMAB

(71) Applicant: Janssen Biotech, Inc., Horsham, PA (US)

(72) Inventors: Daphne Ann Salick Ryan, Manalapan, NJ (US); John Kehoe, Spring House, PA (US); John Wheeler, Spring House, PA (US); Chunlin Yang, Belle Mead, NJ (US); Abla Creasy, Morristown, NJ (US)

(73) Assignee: Janssen Biotech, Inc., Horsham, PA (US)

(*) Notice: Subject to any disclaimer, the term of this patent is extended or adjusted under 35 U.S.C. 154(b) by 0 days.

(21) Appl. No.: 14/338,391

(22) Filed: Jul. 23, 2014

(65) Prior Publication Data

US 2014/0328837 A1 Nov. 6, 2014

Related U.S. Application Data

(62) Division of application No. 13/474,056, filed on May 17, 2012, now Pat. No. 8,822,423.

(51) Int. Cl.
*A61K 47/42* (2006.01)
*C07K 16/24* (2006.01)
*A61K 39/395* (2006.01)
*A61K 39/00* (2006.01)

(52) U.S. Cl.
CPC ............ *A61K 47/42* (2013.01); *A61K 39/3955* (2013.01); *C07K 16/241* (2013.01); *A61K 2039/505* (2013.01); *C07K 2317/24* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,510,418 A | 4/1996 | Rhee et al. |
| 6,187,330 B1 | 2/2001 | Wang et al. |
| 6,472,147 B1 | 10/2002 | Janda et al. |
| 2006/0008532 A1 | 1/2006 | Govardhan et al. |
| 2009/0304719 A1 | 12/2009 | Daugherty et al. |
| 2010/0112070 A1 | 5/2010 | Eliaz et al. |

OTHER PUBLICATIONS

Kosmac, et al., "Exploring the Binding Sites of Anti-Infliximab Antibodies in Pediatric Patients with Rheumatic Diseases Treated with Infliximab," Pediatric Research, 69(3): 243-248 (2011).
Jansson, et al., "All individual domains of staphylococcal protein A show Fab binding," FEMS Immunology Med. Microbiology, 20(1): 69-78 (1998).
Kay, et al., "Screening Phage-Displayed Combinatorial Peptide Libraries," Methods, 24: 240-246 (2001).
Lichtenstein, et al., "Are there Predictors of Remicade Treatment Success or Failure?" Advance Drug Delivery Reviews, 57: 237-245 (2005).
Daugherty, et al., "Formulation and Delivery Issues for Monoclonal Antibody Therapeutics," Advanced Drug Delivery Reviews, 58: 686-706 (2006).
Valat, et al., "Can Sciatica Induced by Disc Herniation be Treated with Tumor Necrosis Factor a Blockage?" Arthritis & Rheumatism, 56 (12): 3887-3895 (2007).
Day, et al., "Anti-TNF-α-Loaded Microspheres as a Prospective Novel Treatment for Crohn's Disease Fistulae," Tissue Engineering, Part C: Methods, 15(5): 855-864 (2010).
Sefton, et al., "Release and Activity of Anti-TNF-Alpha Therapeutics from Injectable Chitosan Preparations for Local Drug Delivery," Journal of Biomedical Materials Research Part B: Applied Biomaterials, 90(1): 319-316 (2009).
Copy of PCT International Search Report dated 01 Nov. 2013.

*Primary Examiner* — David Romeo
(74) *Attorney, Agent, or Firm* — Kirk Baumeister

(57) ABSTRACT

We have disclosed affinity peptides toward infliximab. More specifically we have disclosed an affinity biomatrix where the affinity peptide is covalently attached to a biocompatible, biodegradable polymer. The affinity biomatrix is useful in preparing controlled release devices for infliximab.

8 Claims, 16 Drawing Sheets

FIG. 1.

| | |
|---|---|
| SEQ ID NO: 1 | AGWTVAYVPPGPSYATS |
| SEQ ID NO: 2 | AGYVCDPAGPNCWA |
| SEQ ID NO: 3 | AGTYCHPDQLRNLCPV |
| SEQ ID NO: 4 | AGVTCRMTEYGPMCPT |
| SEQ ID NO: 5 | AGNRCAYAAGTIQCFP |
| SEQ ID NO: 6 | AGEICYWHDTDWVCTE |
| SEQ ID NO: 7 | AGTHCSYVLGRIECLP |
| SEQ ID NO: 8 | AGNYCHPDQLSQFCAR |
| SEQ ID NO: 9 | AGVACHSTGTNIYTCTY |
| SEQ ID NO: 10 | AGVWCGDETLPPSICFR |
| SEQ ID NO: 11 | AGSLCHTVGSGIYNCTK |
| SEQ ID NO: 12 | AGIQCHDVGAGVVTCTY |
| SEQ ID NO: 13 | AGPPCIVTQLSDLSFCAP |
| SEQ ID NO: 14 | AGARCAPAFDANWLICSN |
| SEQ ID NO: 15 | AGPPCAAAMAQAQLACTH |
| SEQ ID NO: 16 | AGVVCATPEWTWDPACAT |
| SEQ ID NO: 17 | AGLLCAPSLDPDYILCDQ |
| SEQ ID NO: 18 | AGLLCEPWPPTAESICRS |
| SEQ ID NO: 19 | AGPPYTVFVHL |
| SEQ ID NO: 20 | AGYCISDYIDPCH |
| SEQ ID NO: 21 | AGPCISDYFDPCH |
| SEQ ID NO: 22 | AGLCPELPHC |
| SEQ ID NO: 23 | AGPCPELPHCTY |

FIG. 6A.

SEQ ID NO: 24   Ac-AGYVCDPAGPNCWA-SGGSGGSGG-Lys(Propargylacetyl)-NH$_2$
SEQ ID NO: 25   Ac-AGVWCGDETLPPSICFR-SGGSGGSGG-Lys(Propargylacetyl)-NH$_2$

FIG. 6B.

SEQ ID NO: 26  Ac-AGYVCDPAGPNCWA-SGGSGGSGG-K-$NH_2$
SEQ ID NO: 27  Ac-AGVWCGDETLPPSICFR-SGGSGGSGG-K-$NH_2$

FIG. 10.

SEQ ID NO: 28  AGLYVSPWPPTAESTAII
SEQ ID NO: 29  AGLYVSPWPPTAESTAVL
SEQ ID NO: 30  AGLHVYPWPPTAESTAYL
SEQ ID NO: 31  AGAYVFPWPPTAESTVTL

AFFINITY PEPTIDES TOWARD INFLIXIMAB

CROSS REFERENCE TO RELATED APPLICATIONS

This application is a divisional of U.S. application Ser. No. 13/474,056, filed 17 May 2012, now U.S. Pat. No. 8,822,423. The entire content of the aforementioned application is incorporated herein by reference in its entirety.

FIELD OF THE INVENTION

The invention relates to specific affinity peptides toward infliximab. In addition, the invention relates the use of these affinity peptides in controlled release devices for infliximab.

BACKGROUND OF THE INVENTION

Infliximab is a chimeric IgG1κ monoclonal antibody, which is a type of protein that recognizes, attaches to, and blocks the action of tumor necrosis factor-alpha (TNF-alpha). Infliximab is currently sold under the tradename REMICADE by Centocor Ortho Biotech, Inc., in Horsham, Pa. Infliximab has been used for the treatment of inflammatory disorders, such as plaque psoriasis, rheumatoid arthritis, psoriatic arthritis, adult Crohn's disease, pediatric Crohn's disease, ulcerative colitis, and ankylosing spondylitis. Currently, infliximab is given by IV infusion and it's half-life is approximately eight weeks. Initially, patients receive three infusions (5 mg/kg) given at 0, 2 and 6 weeks. Following, the patients are dosed (5 mg/kg) every eight weeks. Due to frequent dosing and patient visits to the clinic, the cost associated with infliximab is high.

Therefore, there is a need for a controlled release device for infliximab to eliminate the frequent dosing and doctor visits for the patient and provide a cost effective treatment. Standard methods for preparing controlled release devices include the use of polymeric matrices, typically in the form of microspheres, rods, sheets or pellets, which are used to encapsulate the active agent. A variety of techniques are known by which active agents can be incorporated into polymer matrices. Examples include solvent evaporation, spray drying, emulsification, melt blending and simple physical mixing of particles of discrete size or shape. None of these approaches may be applied to incorporate peptides or proteins into the polymers due to the delicate nature of these molecules. Peptides and proteins are susceptible to denaturation by solvents, by emulsification, by heat and, in particular, by terminal sterilization.

Therefore, there is a need for a method of making a controlled release device for infliximab, where the method does not denature or otherwise inactivate the activity of the protein. A controlled release device for infliximab is also desired which provides a localized, sustained release of the protein, eliminates the need for frequent dosing and doctor's visits for the patient, and provides a cost effective treatment.

SUMMARY OF THE INVENTION

We have described herein specific affinity peptides toward infliximab. These affinity peptides, which have a specific affinity for infliximab, are useful in preparing an affinity biomatrix. Controlled release devices for infliximab are also described which are prepared from the affinity biomatrix and infliximab.

BRIEF DESCRIPTION OF THE FIGURES

FIG. 1. Amino acid sequences of the infliximab affinity peptides, containing linear and disulfide-constrained peptides.

FIG. 6A. Amino acid sequences (SEQ ID NO: 24 and SEQ ID NO: 25) of the alkyne peptides used for the conjugation of SEQ ID NO: 2 and SEQ ID NO: 10 respectively, to the azide-modified collagen matrix using click chemistry.

FIG. 6B. Amino acid sequences (SEQ ID NO: 26 and SEQ ID NO: 27) of the lysine terminated peptides used for the conjugation of SEQ ID NO: 2 and SEQ ID NO: 10 respectively, to the aldehyde functionalized hyaluronic acid matrix using schiff base chemistry.

FIG. 10. Amino acid sequences of the linear fragments of SEQ ID NO: 18 that bind to infliximab.

DETAILED DESCRIPTION OF THE INVENTION

Figure 2A:
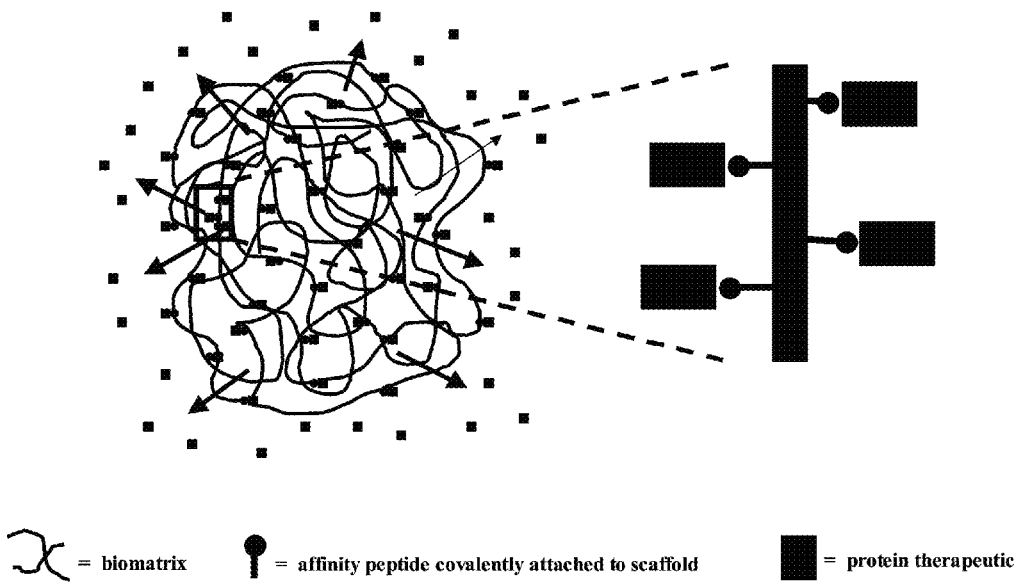
FIG. 2A. Pictorial representation of a controlled release device comprising an affinity biomatrix and infliximab.
Figure 2B:
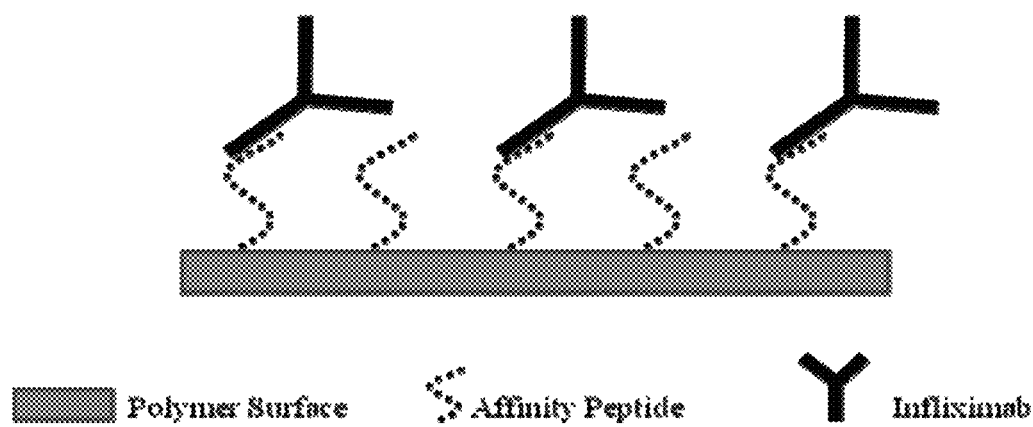
FIG. 2B. Pictorial representation of the surface of a controlled release device comprising an affinity biomatrix and infliximab.

We describe herein, affinity peptides toward infliximab. In one embodiment, the infliximab is an anti-inflammatory, chimeric IgG1κ monoclonal antibody which blocks TNF-alpha receptor binding. Affinity peptide toward infliximab indicates that the peptide has a specific binding affinity toward infliximab. The peptide may be either linear or disulfide constrained. In one embodiment, the affinity peptide toward infliximab is any one of the affinity peptides shown in FIG. 1. In another embodiment, the affinity peptide may be a fragment of any one of the affinity peptides shown in FIG. 1. While the affinity peptide has specific affinity toward infliximab, the affinity peptide does not interfere with the binding of TNF-alpha to infliximab. These affinity peptides are useful in the preparation of controlled release devices for infliximab.

The affinity peptides toward infliximab shown in FIG. 1 were identified using a pIX phage display technology described in U.S. Pat. No. 6,472,147. Primary peptide phage libraries with high complexity ($10^9$ peptides sequences per library) were used to select for affinity peptides toward infliximab. More specifically, biotinylated-infliximab was immobilized on a streptavidin-coated ELISA plate and phage which display the peptide sequences on the pIX minor coat protein were introduced. The phage that did not bind to infliximab were washed away and the phage that did bind to infliximab were isolated and amplified. The isolated phage that bound to infliximab were used as input for the second round of the selection following the procedure stated above for a total of three rounds. At the end of the third round the phage that bound to infliximab were sequenced to determine the peptide which is responsible for binding to infliximab. Peptides having affinity toward infliximab are listed in FIG. 1.

The affinity peptides toward infliximab are useful in preparing an affinity biomatrix. The affinity biomatrix is prepared by covalently attaching at least one affinity peptide toward infliximab, as described above, to a biocompatible, biodegradable polymer. The affinity biomatrix may be prepared such that the affinity peptide toward infliximab is present in the bulk of the polymer, on the surface of the polymer, or both in the bulk of the polymer and on the surface of the polymer. Furthermore, the affinity biomatrix is useful as a controlled release device for infliximab. Representative embodiments of controlled release devices are shown pictorially in FIG. 2A and FIG. 2B. The controlled release device for infliximab comprises an affinity biomatrix and infliximab.

The biocompatible, biodegradable polymer used to prepare the affinity biomatrix may be natural polymers, synthetic polymers, and combinations thereof. The biodegradable polymers readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that no permanent trace or residual of the segment is retained by the body.

Suitable natural polymers include, but are not limited to proteins such as, collagen, elastin, keratin, silk, glucosaminoglycans (GAGs), thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, and atelocollagen; polysaccharides such as, starch, pectin, cellulose, alkyl cellulose (e.g. methylcellulose), alkylhydroxyalkyl cellulose (e.g. ethylhydroxyethyl cellulose), hydroxyalkyl cellulose (e.g. hydroxylethyl cellulose), cellulose sulfate, salts of carboxymethyl cellulose, carboxymethyl cellulose, carboxyethyl cellulose, chitin, carboxymethyl chitin, hyaluronic acid, salts of hyaluronic acid, alginate, cross-linked alginate alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyglucuronic acid), and derivatives; polynucleotides such as, ribonucleic acids, deoxyribonucleic acids, and combinations thereof.

In one embodiment the natural polymer is collagen. In yet another embodiment the natural polymer may be obtained from decellularized tissue. The decellularized tissue may be obtained from autogeneic tissue, allogeneic tissue or xenogeneic tissue. Suitable decellularized tissues include, but are not limited to skin, omentum, periosteum, perichondrium, synovium, fascia, mesenter, bone, sinew, and the like. In another embodiment, the natural polymer is a polysaccharide. In yet another embodiment, the polysaccharide is hyaluronic acid.

Examples of suitable synthetic polymers include, but are not limited to aliphatic polyesters, poly(amino acids), copoly(ether-esters), polyalkylene oxalates, polyamides, poly(iminocarbonates), polyorthoesters, polyoxaesters, polyamidoesters, polyoxaesters containing amine groups, poly(anhydrides), polyphosphazenes, biomolecules and blends thereof. For the purpose of this invention aliphatic polyesters include, but are not limited to homopolymers and copolymers of lactide (which includes lactic acid, d-, l- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof.

Suitable aliphatic polyesters include, but are not limited to homopolymers and copolymers of lactide (which includes lactic acid, D-,L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

In one embodiment, the biocompatible, biodegradable polymer and the affinity peptides toward infliximab have suitable reactive groups and corresponding functional groups to covalently attach the affinity peptide to the polymer. The reactive groups and functional groups may be on the polymer, the affinity peptide, and combinations thereof. Suitable reactive groups include, but are not limited to aryl azide, carbodiimide, hydrazine, hydroxymethyl phosphine, imidoester, isocyanate, carbonyl, maleimide, NHS-ester, PFP-ester, thiol, pyridyl disulfide and/or vinyl sulfone and the like. Suitable functional groups include, but are not limited to hydroxyl, carboxyl, aldehyde, ester, thiol, amine, alkene, alkyne, alkyl halide, hydrazine and/or azide functional groups. One of skill in the art of organic chemistry or polymer chemistry would be able to functionalize the affinity peptide and the polymer with the above suitable reactive groups and corresponding functional groups to covalently attach the affinity peptide to the polymer. For example, in the case of collagen the amine functional groups on the lysine residues displayed from collagen can be coupled to the C-terminal carboxyl group of an affinity peptide using simple carbodiimide chemistry. Alternatively, in the case of hyaluronic acid the amine functional groups on the lysine residues displayed from the affinity peptide can be coupled to hyaluronic acid by using simple oxidation chemistry.

Optionally, a linker sequence may be added to the peptides shown in FIG. 1 in order to increase the availability of the affinity peptide to bind to infliximab. The linker sequence can be $(SGG)_n$ or $(XXX)_n$, where X may be any combination of serine, glycine, alanine or threonine. In one embodiment, the number of repeat units n is from about 1 to about 10. In another embodiment, the number of repeat units n is from about 3 to about 5.

For example, the affinity biomatrix may be prepared from soluble and/or fibrillar Type I bovine collagen. Briefly, a homogenized collagen suspension in water, having a concentration of from about 10 mg/mL to about 100 mg/mL, is cast into a mold and then lyophilized. After a thermal dehydration step, the affinity peptides are conjugated to the collagen using 1-ethyl-3-[3-dimethylaminopropyl]carbodiimide hydrochloride (EDC)/N-hydroxysulfosuccinimide (Sulfo-NHS) coupling chemistry. Alternatively, after a thermal dehydration step and functionalization of the collagen with an azide, alkyne-modified affinity peptides are conjugated to the collagen with a copper catalyst. The collagen affinity biomatricies prepared by the methods described above are in the form of a porous three-dimensional foam scaffold.

Alternatively, the affinity biomatrix may be prepared from hyaluronic acid. For example, the 1,2 diol in the hyaluronic acid sugar ring is first oxidized to an aldehyde, using sodium periodate. Next, an affinity peptide toward infliximab that has been conjugated to provide a lysine residue (amine) is reacted with the aldehyde group on the hyaluronic acid to form a Schiff base. The Schiff base is further reacted with a reducing agent, such as sodium cyano-borohydride to provide the crude affinity biomatrix. The affinity biomatix may be purified while in solution by dialysis, and isolated by lyophylization. The lyophilized affinity biomatrix may then be reconstituted, if desired.

The affinity biomatrix is useful as a controlled release device for infliximab. The controlled release device for infliximab comprises an affinity biomatrix and infliximab. The amount of infliximab that may be loaded into the affinity biomatrix is dependent upon the amount of affinity peptide conjugated to the biocompatible, biodegradable polymer. The amount of affinity peptide present on the biocompatible, biodegradable polymer may be equal to or greater than the desired amount of infliximab in the controlled release device. Therefore there may be at least 1 mole of affinity peptide to 1 mole of infliximab to be delivered. One of skill in the art will be able to determine how much infliximab is needed in the controlled release device for the desired anti-inflammatory response. The controlled release device may be in the form of sponges, particles, injectable gels or liquids, membranes, films, fibers and fiber based scaffolds, and the like.

In one embodiment, the controlled release device is in the form of an injectable gel or liquid, where the affinity biomatrix is in an aqueous solution and contains infliximab. Examples of suitable aqueous solutions include, but are not limited to physiological buffer solution, saline, water, buffered saline, phosphate buffer solution, Hank's balanced salts solution, PBS, Tris buffered saline, Hepes buffered saline, and mixtures thereof. Polymers useful for preparing an injectable gel or liquid device may be selected from the natural or synthetic polymers described above. In the case of an injectable liquid or gel, the affinity biomatrix may be present in the aqueous solution in the amount of from about 10 mg/mL to about 150 mg/mL.

The infliximab controlled release device may optionally have disinfectant and/or antibacterial agents incorporated therein. Suitable agents include, but are not limited to, antimicrobial peptides, quaternary ammonium salts, azide, silver, vancomycin, tobramycin, cefamandol, cephalothin, carbenicillin, amoxicillin, gentamicin, and combinations thereof. The infliximab controlled release device may also optionally have cells incorporated therein. Suitable cell types include, but are not limited to, chondrocytes, osteocytes, osteoblasts, stem cells, pluripotent cells, umbilical cord cells, stromal cells, mesenchymal stem cells, bone marrow cells, embryonic stem cells; precursor cells derived from adipose tissue; peripheral blood progenitor cells; stem cells isolated from adult tissue; genetically transformed cells; and combinations thereof. The controlled release device for infliximab can be sold as a kit containing a sterile affinity biomatrix and sterile lyophilized powder of infliximab. The affinity biomatrix and infliximab contained in the kit can be sterilized using conventional sterilization procedures which may include, but are not limited to e-beam, gamma irradiation and aseptic sterile preparation methods.

The infliximab affinity biomatrix may have many applications/indications which include the following. First, the affinity biomatrix may be used for the localized, sustained release of infliximab for the treatment of inflammatory degenerative connective diseases associated with TNF-$\alpha$, such as osteoarthritis, degenerative intervertebral disc degeneration, and the like. Infliximab will help to suppress the inflammatory reaction and further degeneration. Additionally, the affinity biomatrix can be used for the localized, sustained release of infliximab for the treatment of inflammatory disorders including plaque psoriasis, rheumatoid arthritis, psoriatic arthritis, adult Chrohn's disease, pediatric Crohn's disease, fistulizing Chrohn's disease, ulcerative colitis, and ankylosing spondylitis. The affinity biomatrix may also be used for the localized, sustained release of infliximab for adhesion prevention, topical applications for the treatment of chronic wounds, and as a tissue repair device.

The controlled release device for inflixmab allows one to locally deliver infliximab in a controlled manner. The containment of infliximab in the biomatrix will help to increase the half-life of the therapeutic and thus, decrease dosing frequencies and cost.

EXAMPLES

Example 1

Infliximab Affinity Peptide Selection using Phage Display

Primary peptide phage libraries with high complexity ($10^9$ peptides sequences per library) were used to select for affinity peptides toward infliximab. More specifically, biotinylated-infliximab was immobilized on streptavidin-coated magnetic beads and phage which display the peptide sequences on the pIX minor coat protein were introduced. The phage that did not bind to infliximab were washed away and the phage that did bind to infliximab were isolated and amplified. The isolated phage that bound to infliximab were used as input for the second round of the selection following the procedure stated above for a total of three rounds.

Prior to starting the solution based panning, all plasticware was blocked with 3% milk in tris buffered saline containing Tween 20 (TBST) and allowed to incubate at 4° C. overnight. Streptavidin-coated magnetic beads sold under the tradename DYNABEADS M280 by Invitrogen, Grand Island, N.Y., (cat #602.10) were washed three times with phosphate buffered saline (PBS). Next, the beads were loaded with biotinylated infliximab at a concentration of 150 micrograms per milliliter. Infliximab was obtained from Janssen Pharmaceuticals, Inc., Radnor, Pa. After loading, the infliximab-coated magnetic beads were washed three times with PBD then blocked with 3% milk in TBST for one hour at room temperature. Meanwhile, eppendorf tubes were blocked (one per library) using 1 mL of 3% dehydrated milk in TBST. Two MC1061F' GII *E. coli* cultures were started in 2xYT media supplemented with tetracycline on a shaker at 37° C. Next, the phage libraries were blocked prior to the selection. The blocking solution in the eppendorf tubes was then discarded and replaced with 200 microliters of the respective phage library and 800 microliters of 3% milk in TBST. The libraries were allowed to block with tumbling at room temperature for one hour. To start the selection, 1 milliliter of resin was captured using a magnet and 1 milliliter of the respective blocked phage library was introduced. This was allowed to tumble at room temperature for one hour. The volume for each panning round was kept constant at 1 milliliter. To remove any loosely bound phage, the phage-bound, infliximab coated magnetic beads were washed manually with PBS containing 0.05% Tween-20 for a total of two washes followed by one wash with PBS. Following the last wash, 600 microliters of mid-log phage MC1061F' GII *E. coli* were introduced to each eppendorf tube. The beads were then resuspended using gentle inversions and incubated at 37° C. for 30 minutes. The infected bacteria were grown for 4 hours at 37° C. in 50 mL of 2xYT media supplemented with tetracycline. Next, the bacteria were separated by centrifugation and phage were precipitated using a PEG/NaCl solution. The PEG-precipitated phage were used in round two and the above process was repeated for a total of three cycles of the selection process.

At the end of the third round the phage that bound to infliximab were sequenced to determine the peptide which is responsible for binding to infliximab. The phage-infected bacteria were plated out for single plaques in top agar with MC1061F'GII *E. coli*. The resultant plaques were used to isolate phage that bind to infliximab using ELISA. Once single phage were identified, the phage that bound to infliximab were amplified, PEG-precipitated and sequence analysis was performed. Peptides having affinity toward infliximab are listed in FIG. 1.

These phage were used for the phage titration described in Example 2 and the confirmatory and cross-reactivity phage ELISA assay described in Example 3.

Example 2

Infliximab Selection Output Phage Titration

A phage titration was performed to determine the concentration of phage which resulted from the PEG precipitation of the phage that bound to infliximab described in Example 1.

*E. coli* MC1061F'GII were grown in 2xYT media supplemented with tetracycline for 2-3 hours at 37° C. on a shaker (180-250 rpm). In a 96-well plate, phage dilutions were performed, assuming the PEG precipitated stock solutions contain $10^{12}$ phage/mL.

Briefly, 100 microliters of 2xYT media was introduced to the wells of a 96-well plate. To column 1, 10 microliters of respective phage stock solutions were introduced. Serial 1:10 dilutions were performed across the plate to column 12 resulting in phage concentrations of $10^{10}$, $10^9$, $10^8$, $10^7$, $10^6$, $10^5$, $10^4$, $10^3$, $10^2$, $10^1$, $10^0$, $10^{-4}$, respectively, where each row contains a distinct phage. For phage plaque growth, 1.5 microliters of each respective phage dilution series was introduced to an LB/Tetracycline/X-Gal agar plate coated with a solidified top agar/bacteria suspension. Plates were incubated upside down at 37° C. overnight. After overnight incubation, a dilution was chosen where the phage plaques are well separated and can be counted. The following formula was used to calculate the titer: (# plaques)(66.7)($10^{ddilution\ number-1}$)×100=phage/mL, where 66.7 is the dilution factor of the phage in each well and the dilution number is the number of dilutions performed until phage plaques could be counted. Multiplication by 100 yields the number of phage/mL in the stock phage suspension.

Calculated phage numbers are shown in Table 1. Phage concentrations obtained were used to perform the dilutions for the confirmatory and cross-reactivity phage ELISA assay described in Example 3.

TABLE 1

| SEQ ID NO. | Phage/mL |
|---|---|
| 1 | $3.3 \times 10^{13}$ |
| 2 | $3.3 \times 10^{13}$ |
| 3 | $4.0 \times 10^{12}$ |
| 4 | $1.4 \times 10^{12}$ |
| 5 | $1.4 \times 10^{12}$ |
| 6 | $1.4 \times 10^{12}$ |
| 7 | $1.4 \times 10^{12}$ |
| 8 | $1.4 \times 10^{12}$ |
| 9 | $1.4 \times 10^{12}$ |
| 10 | $1.4 \times 10^{12}$ |
| 11 | $1.4 \times 10^{12}$ |
| 12 | $1.4 \times 10^{12}$ |
| 13 | $1.2 \times 10^{12}$ |
| 14 | $1.0 \times 10^{12}$ |
| 15 | $1.2 \times 10^{12}$ |
| 16 | $1.0 \times 10^{12}$ |
| 17 | $1.2 \times 10^{12}$ |
| 18 | $1.2 \times 10^{12}$ |
| 19 | $1.3 \times 10^{11}$ |
| 20 | $6.0 \times 10^{12}$ |
| 21 | $6.0 \times 10^{12}$ |
| 22 | NA (Did not titer) |
| 23 | $5.3 \times 10^{13}$ |

Example 3

Confirmatory and Cross-Reactivity Phage Enzyme Linked Immunosorbent Assay (ELISA)

In this experiment, we are confirming the binding of the phage identified in Example 1 to infliximab. In addition, we are also testing that the phage do not exhibit significant binding to monoclonal antibody (mAb) competitor, human IgG, human serum albumin (HSA) and collagen.

96-well black ELISA plates were coated with streptavidin (Columns 1 through 4), mAb competitor (Columns 5 and 6), hIgG (Columns 7 and 8), human serum albumin (Columns 9 and 10) and collagen (Columns 11 and 12), at a concentration of 5 micrograms/mL in PBS. Plates were incubated overnight at 4° C. Plates were washed 3 times with TBST using a plate washer. To the streptavidin-coated wells in columns 3 and 4, 100 microliters of a 5 micrograms/mL solution of biotinylated-infliximab was introduced and allowed to sit at room temperature for 30 minutes. To all other wells, 100 microliters of PBS was introduced. The plates were again washed 3 times with TBST using the plate washer. The wells were then blocked with 250 microliters of a 3% dehydrated milk suspension in TBST and allowed to sit at room temperature for a minimum of 1 hour. Using phage concentrations determined by the phage titrations, dilutions of the phage stock solutions were performed in a separate 96-well plate to result in phage concentrations of $10^{10}$, $10^9$, $10^8$, $10^7$, $10^6$ and $10^5$ phage/well. After blocking, the ELISA plate was washed 3 times with TBST and 100 microliters of the phage dilutions were introduced to the respective ELISA plates and allowed to sit at room temperature for a minimum of 1 hour. The ELISA plate was again washed 3 times with TBST using the plate washer and 100 microliters of an horseradish peroxidase (HRP)-conjugated Anti-M13 Phage Mab (1:5000 dilution in PBS) was introduced to each well. The plates were allowed to sit at room temperature for 1 hour after which time the plates were washed 3 times with TBST. Next, a peroxidase-based (POD) HRP-substrate was introduced to each well. The luminescence was read using a luminometer set with a gain of 150.

Figure 3:
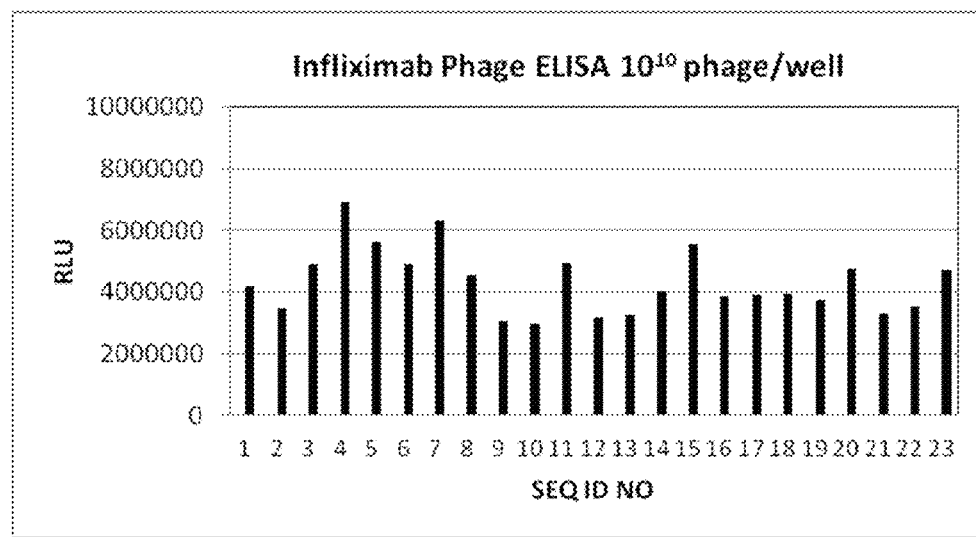
FIG. 3. Infliximab phage ELISA assay confirming that the phage-displayed peptides generated from the phage selection bind to infliximab.
Figure 4A:
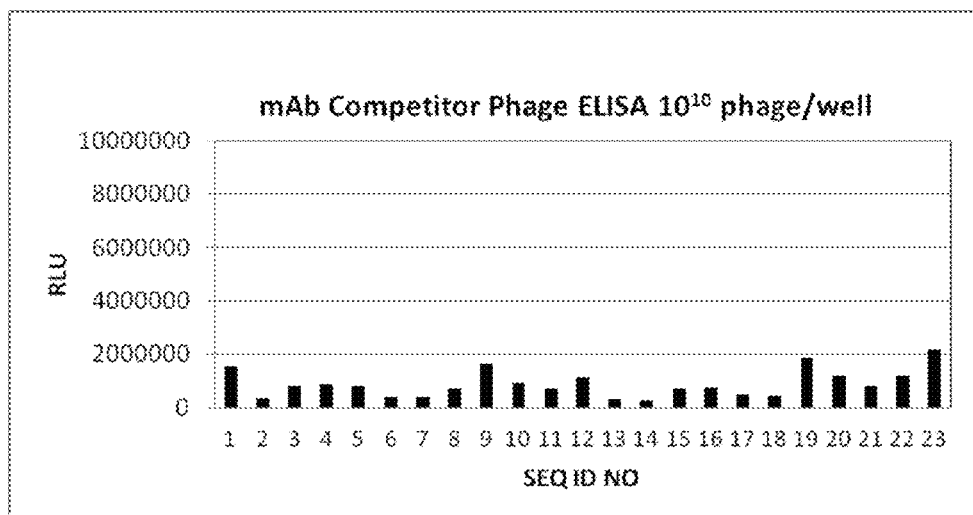
FIG. 4A. Cross-reactivity phage ELISA assays toward mAb competitor.
Figure 4B:
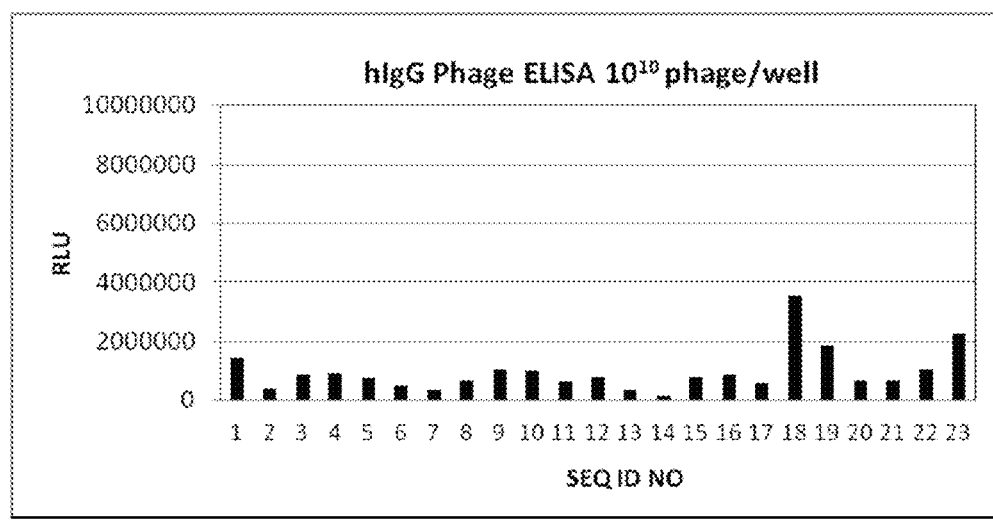
FIG. 4B. Cross-reactivity phage ELISA assays toward human IgG.
Figure 4C:
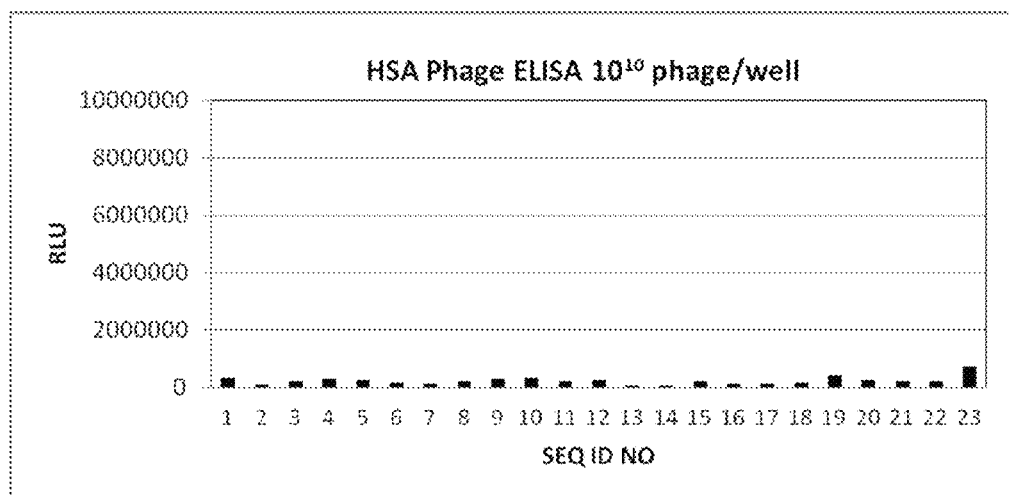
FIG. 4C. Cross-reactivity phage ELISA assays toward human serum albumin (HSA).
Figure 4D:
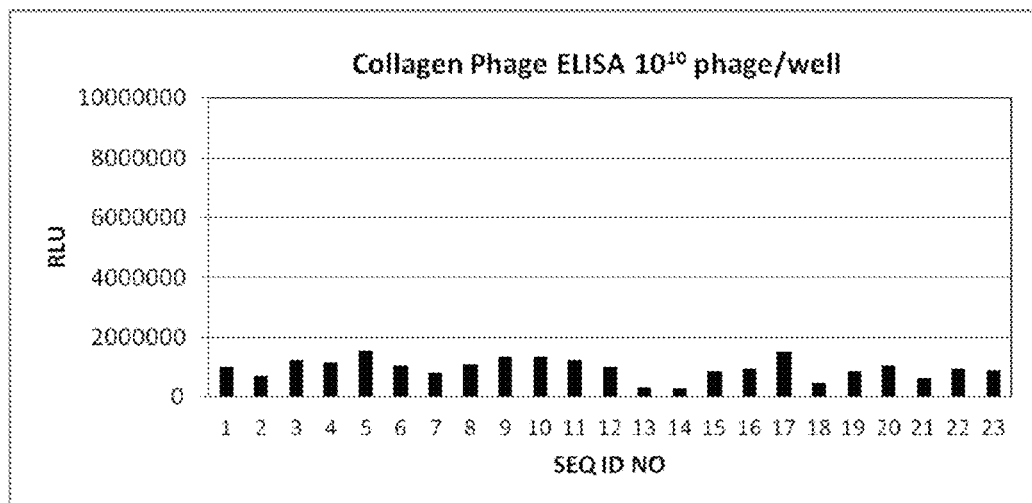
FIG. 4D. Cross-reactivity phage ELISA assays toward collagen.

The phage ELISA data in FIG. 3 and FIG. 4 show relative luminescence and have an N value of 2. Data in FIG. 3 confirms the binding of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 to infliximab. Data in FIG. 4A, FIG. 4B, FIG. 4C and FIG. 4D show that the phage are minimally cross-reactive with mAb competitor, hIgG, HSA and collagen, respectively.

Example 4

Infliximab Affinity Peptide ELISA Assay

Concentration dependent binding efficiency of infliximab to the affinity peptides was evaluated using ELISA.

96-well black ELISA plates were coated with goat anti-human Fc (Jackson Immunoresearch Laboratories, Inc., West Grove, Pa., cat. #109-006-098) at a concentration of 5 micrograms/mL in PBS. Plates were incubated overnight at 4° C. Plates were washed 3 times with TBST using a plate washer. To the anti-Fc-coated wells, 100 microliters of a 20 micrograms per milliliter solution of infliximab was introduced and allowed to sit at room temperature for one hour. To all other wells, 100 microliters of PBS was introduced. The plates were again washed 3 times with TBST using the plate washer. The wells were then blocked with 250 microliters of a 3% dehydrated milk suspension in TBST and allowed to sit at room temperature for a minimum of 1 hour. Biotinylated, chemically synthesized peptides having SEQ ID NO: 2, SEQ ID NO: 3, SEQ ID NO: 10, and SEQ ID NO: 13 were prepared using standard, automated Fluorenylmethyloxycarbonyl (Fmoc) solid phase peptide synthesis procedures. Each peptide solution for the assay was prepared from a 500 micromolar stock solution. The stock solution was serially diluted in assay buffer resulting in peptide concentrations of 500, 166.6, 55.5, 18.5, 6.2, 2.1, 0.69, 0.23, 0.076, 0.025, 0.0085 and 0.0028 micromolar.

After blocking, the ELISA plate was washed 3 times with TBST and 100 microliters of the serially diluted peptides were added to the corresponding wells of the ELISA plate and allowed to sit at room temperature for a minimum of 1 hour. The ELISA plate was again washed 3 times with TBST using the plate washer and 100 microliters of HRP-conjugated streptavidin (1:10000 dilution in PBS) was introduced to each well. The plates were allowed to sit at room temperature for 1 hour after which time the plates were washed 3 times with TBST. Next, a POD HRP-substrate was introduced to each well. The luminescence was read using a luminometer set with a gain of 150.

Figure 5:
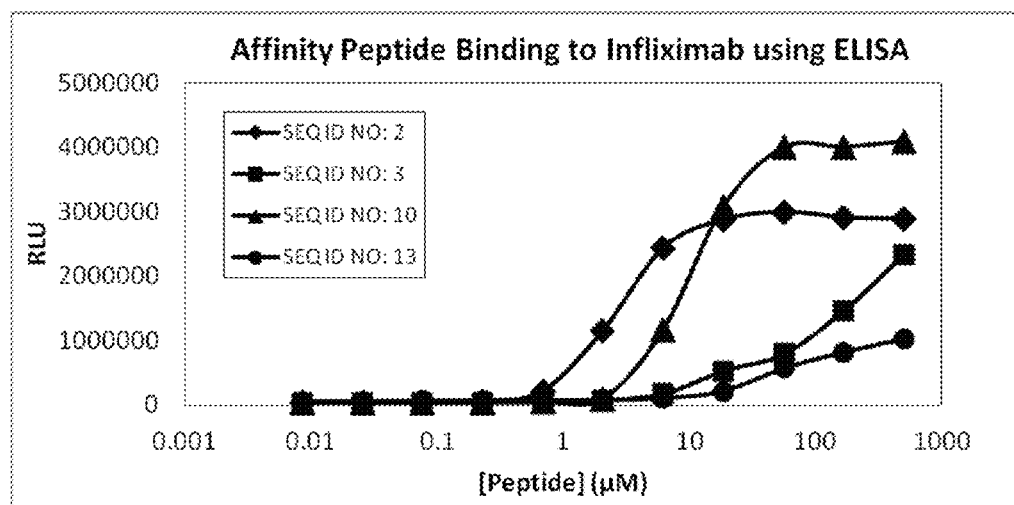
FIG. 5. Concentration dependent affinity peptide binding to infliximab determined using ELISA.

The ELISA data in FIG. 5 was normalized to molar concentration based on the molecular weights of the peptide sequences. The data in FIG. 5 shows the concentration-dependent binding of the peptides to infliximab. Peptide sequences were ranked according to their concentration-dependent binding to infliximab as follows; SEQ ID NO: 2>SEQ ID NO: 10>SEQ ID NO: 3>SEQ ID NO: 13.

Example 5

Surface Plasmon Resonance

Peptide binding affinity to infliximab was evaluated for SEQ ID NO: 2 and SEQ ID NO: 10 by surface plasmon resonance measurements. Measurements were performed on a surface plasmon resonance-based biosensor sold under the tradename BIACORE S51 (Biacore Life Sciences, Piscataway, N.J.) using a streptavidin Series-S sensor chip. Biotinylated peptides were immobilized on the sensor chip at a concentration of 0.1 and 0.2 micrograms/mL (For SEQ ID NO: 8 and SEQ ID NO: 10, c=1 and 10 micrograms/mL). Infliximab was flowed over the affinity peptide functionalized chip at concentrations of 0, 0.78, 1.56, 3.125, 6.25, 12.5, 25, 50 and 100 nM and changes in the refractive index were recorded. Data were fit to a 1:1 Langmuir binding model using analysis software sold under the tradename BIACORE by Biacore Life Sciences, Piscataway, N.J.

The data shown in Table 1 are average equilibrium dissociation constants with an N value of 2. Data show average equilibrium dissociation constants between 9 and 18 nM.

TABLE 1

| | $K_D$ (M) |
| --- | --- |
| SEQ ID: 2 (1011A) | $17.1 \times 10^{-9}$ |
| SEQ ID: 10 (1067B) | $9.17 \times 10^{-9}$ |

Example 6

Preparation of Collagen Biomatrix

A 40 mg/mL solution of 80% fibrous Type I collagen (32 mg) and 20% soluble Type I collagen (8 mg) in water was stirred overnight at 4° C. This suspension was then homogenized in a blender for 3 cycles (30 seconds to 1 min/cycle). Approximately 5 mL of the suspension was transferred to a mold with the dimensions of 5 cm×5 cm and a height of 0.5 cm. The collagen mixture was leveled with a straight edge spatula to ensure an even height distribution of the collagen. Next, the sample was degassed then lyophilized using the cycle shown in Table 3. The samples were then thermally dehydrated using a temperature controlled vacuum chamber. The foam collagen biomatrix was then cut into 6 mm discs using a biopsy punch and stored at room temperature under dry nitrogen purge. The biomatrices prepared in this example were used for functionalization as described in Example 7.

TABLE 3

| Temperature (° C.) | Time (minutes) | Pressure (mTorr) |
| --- | --- | --- |
| −40 | 60 | 500 |
| −25 | 300 | 100 |
| −20 | 600 | 50 |
| −10 | 300 | 50 |
| −5 | 180 | 50 |
| 0 | 120 | 50 |
| 10 | 120 | 50 |
| 20 | 120 | 50 |

Example 7

Preparation of the Azide-Modified Collagen Biomatrix

To prepare the azide-modified collagen biomatrix, a 6 mm collagen sponge disc, prepared as described in Example 6, was placed in 1 mL of 50 millimolar borate buffer in an eppendorf tube and allowed to swell for 1 hour at room temperature. The sponge was removed from the above buffer and placed in 1.5 mL of fresh 50 millimolar borate buffer containing 5 millimolar of the NHS-PEG4-Azide (Thermo Fisher Scientific, Waltham, Mass., cat #26130). The reaction mixture was allowed to tumble at room temperature overnight (approximately 16-18 hours). The sponge was then removed from the reaction mixture and gently squeezed to remove excess fluid. The sponge was then washed using 10 milliliters of PBS while tumbling at room temperature for two hours. The washing process was repeated for a total of three washes. The azide-modified biomatrices described in this example were used to conjugate the affinity peptides as described in Example 8.

Example 8

Conjugation of Infliximab Affinity Peptide to Azide-Modified Collagen Biomatrix For peptide conjugation, a 6 mm collagen sponge disc, prepared as described in Example 7, was placed in 1.8 mL of 20% DMSO/$H_2O$ in an eppendorf tube and tumbled for 30 min. at room temperature. The sponge was removed from the above buffer and placed in 1.8 mL of fresh 20% DMSO/$H_2O$ containing 1 milliolar affinity conjugation peptide. The affinity biomatricies were prepared with affinity conjugation peptide of SEQ ID NO: 2 and SEQ ID NO: 10 (sequences SEQ ID NO: 24 and SEQ ID NO: 25 shown in FIG. 6A), respectively. Peptides were prepared using standard, automated Fluoroenylmethyloxycarbonyl (Fmoc) solid phase peptide synthesis procedures. The sample was tumbled at room temperature for 1 hour. Next, 36 microliters of a 10 millimolar copper acetate 50 millimolar ascorbic acid solution in water was introduced to each eppendorf containing a collagen sponge. This was then tumbled for 2 days at room temperature. Next, the sponge was rinsed by tumbling in 10 mL of PBS for 2 hours. This was repeated for a total of three rinse cycles. Lastly, the sponge was removed from the PBS and allowed to dry on the lyopholizer overnight. Three control samples were also used in the above procedure. 1=Collagen Sponge+Buffer, 2=Collagen Sponge+Peptide/Buffer, and 3=Collagen Sponge+Copper Acetate/Ascorbic Acid. For all samples, the supernatants were lyophilized to a dry powder and analyzed using RP-Analytical HPLC. Data show approximately 10-30% conjugation efficiency was achieved.

Example 9

Conjugation of Infliximab Affinity Peptide to HA Biomatrix

A hyaluronic acid (HA) hydrogel solution (20 mg/mL in PBS), was diluted with sterile filtered water to a final concentration of 2 mg/mL. This solution was allowed to stir at room temperature for 15 minutes. For the activation of HA, a 100 mM sodium periodate solution in water was introduced to the diluted HA solution to a final concentration of 10 mM. The solution was then covered with aluminum foil and allowed to stir at room temperature for 30 minutes. Next, a 1M solution of D-Mannitol in water was introduced to a final concentration of 0.1 M and was allowed to stir at room temperature for 10 minutes. The activated HA was then dialyzed in water using a 3.5K dialysis cassette. The water was changed every two hours for a total of two cycles and then dialysis was performed overnight at room temperature. After dialysis, the water was removed from the sample by lyopholization. For the conjugation of the affinity peptide (sequences shown in FIG. 6B) to the activated HA, 20 mg of activated HA was introduced to 5 mL of sterile filtered water resulting in a 4 mg/mL activated HA solution. In a separate vial, 5 mg of affinity peptide (SEQ ID NO: 26 or SEQ ID NO: 27) was dissolved in 5 mL of 20 mM sodium phosphate buffer (pH 7.5) resulting in a 1 mg/mL peptide solution. Next, a 1:1 dilution of activated HA and peptide was performed (total volume=10 mL) resulting in a 2 mg/mL activated HA:0.5 mg/mL peptide solution. This was allowed to stir at room temperature for four hours. Next, sodium cyanoborohydride was introduced at a final concentration of 5 mM and allowed to stir at room temperature for 30 minutes. The solution was then dialyzed in water and lyophilized to obtain the purified affinity biomatrix.

Example 10

In vitro bioactivity of Infliximab in the Presence of the Affinity Peptides

In this experiment, we determined if the affinity peptides would interfere with the binding of tumor necrosis factor alpha (TNF-α) using WEHI-13VAR mouse fibroblasts. The cell viability was monitored the presence of infliximab with and without affinity peptides using the 3-(4,5-Dimethylthiazol-2-yl)-2,5-diphenyltetrazolium bromide (MTT) assay.

WEHI-13VAR cells (mouse fibroblast cell line) were plated out in wells of a 96 well plate two hours prior to running the experiment at 50000 cells per well. A stock solution of 20 nanograms per milliliter recombinant human TNF-α (R&D Systems, 210-TA/CF) was prepared in culture media containing 7.5 micrograms per milliliter of actinomycin D. Serial dilutions of infliximab were prepared in a concentration range of 0-66 nanomolar in the presence or absence of peptides SEQ ID NO: 2, SEQ ID NO: 10 and SEQ ID NO: 13 at a constant concentration of 66 nanomolar resulting in peptide:infliximab ratios of 1, 4, 16, 64, 256, 1024, 4094 and 16384. 160 microliters of the respective infliximab: peptide solution and 40 microliters of the TNF-α solution were preincubated for 30 minutes prior to the addition to the wells containing the WEHI-13VAR cells. Next, cells were stimulated with 50 microliters of the TNF-α:infliximab:peptide solution and allowed to incubate overnight in a humidified incubator at 37 degrees Celcius with 5% $CO_2$. After overnight incubation, cell viability was assessed using an MTT cell viability assay (R&D Systems, Inc., Minneapolis, Minn. cat #4890-050-K) following the product insert.

Figure 7:
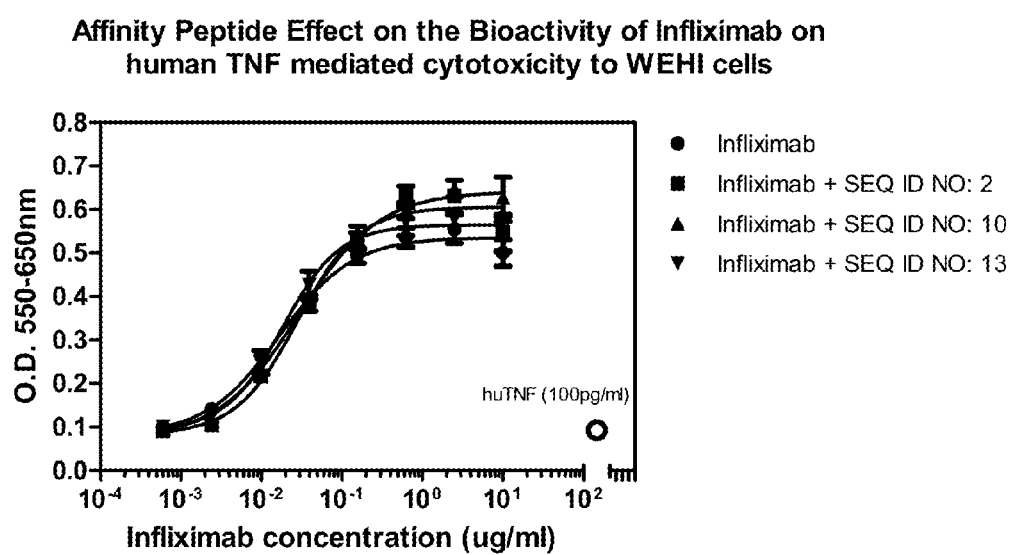
FIG. 7. Functional interference of affinity peptides on infliximab TNF-alpha binding by assessment of viability of mouse WEHI cells after 24 hour incubation in the presence of infliximab.

FIG. 7 shows that SEQ ID NO: 2, SEQ ID NO: 10 and SEQ ID NO: 13 have minimal effect on the viability of WEHI-13VAR mouse fibroblasts in the presence of infliximab. This suggests that SEQ ID NO: 2, SEQ ID NO: 10 and SEQ ID NO: 13 do not interfere with the bioactivity of infliximab.

Example 11

In vitro Release of Infliximab from Collagen Discs

In this experiment, we have evaluated the in vitro controlled release of infliximab from the affinity biomatrix under simulated physiological conditions. For the release studies, 6 mm diameter discs of affinity biomatrix as prepared by the methods described in Example 6, Example 7, and Example 8, were placed in a well of a 24 well cell culture plate. The sponges were loaded with either 50 micrograms or 200 micrograms of infliximab and allowed to sit at room temperature for 60 minutes. A 6 mm diameter disc of the affinity peptide-free collagen as prepared in Example 6 was used as a control. The loaded collagen sponges were then transferred to a well of a 24 well cell culture plate containing 1.5 mL of PBS supplemented with heat denatured fetal bovine serum (FBS) at a concentration of 1 mg/mL. At the respective time points, the media was removed and transferred to an eppendorf tube then stored at 4° C. until analysis. The wells containing the collagen discs were replenished with 1.5 mL of fresh 2% FBS in PBS. The release media was analyzed for infliximab content using ELISA.

Figure 8A:
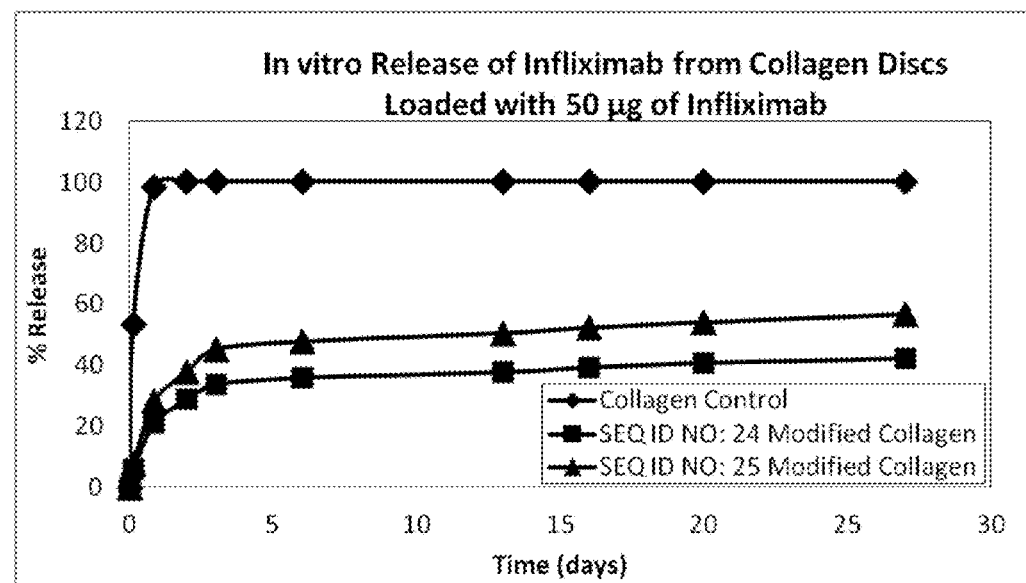
FIG. 8A. In vitro release study, performed in phosphate buffered saline (PBS) containing 2% heat inactivated fetal bovine serum (FBS), showing the amount of infliximab released from the collagen biomatrix and collagen affinity biomatrix discs over a time period of 34 days. (Initial loading concentration=200 micrograms)
Figure 8B:
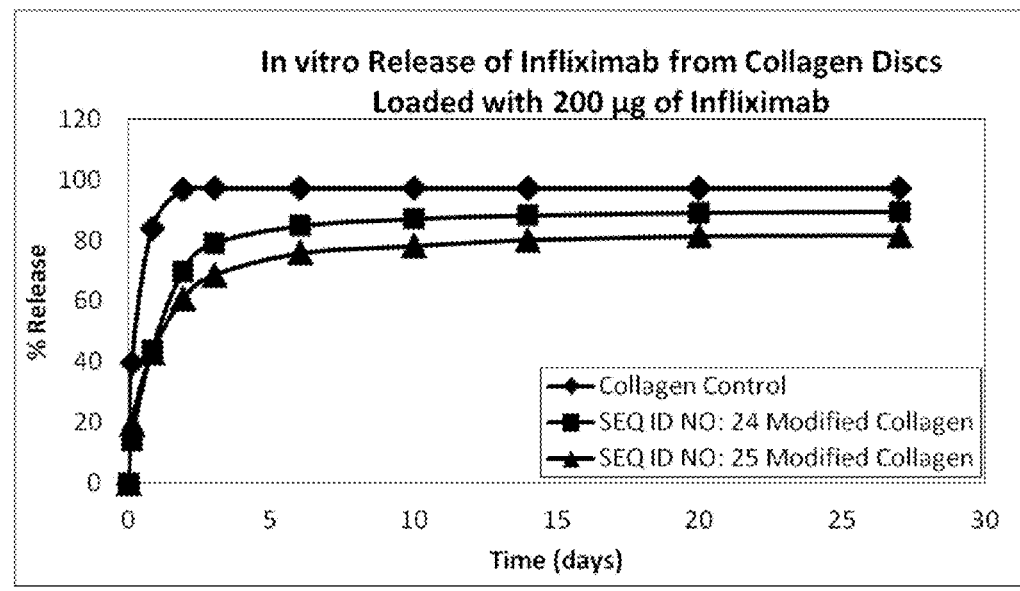
FIG. 8B. In vitro release study, performed in phosphate buffered saline (PBS) containing 2% heat inactivated fetal bovine serum (FBS), showing the amount of infliximab released from the collagen biomatrix and collagen affinity biomatrix discs over a time period of 34 days. (Initial loading concentration=50 micrograms)
Figure 9:
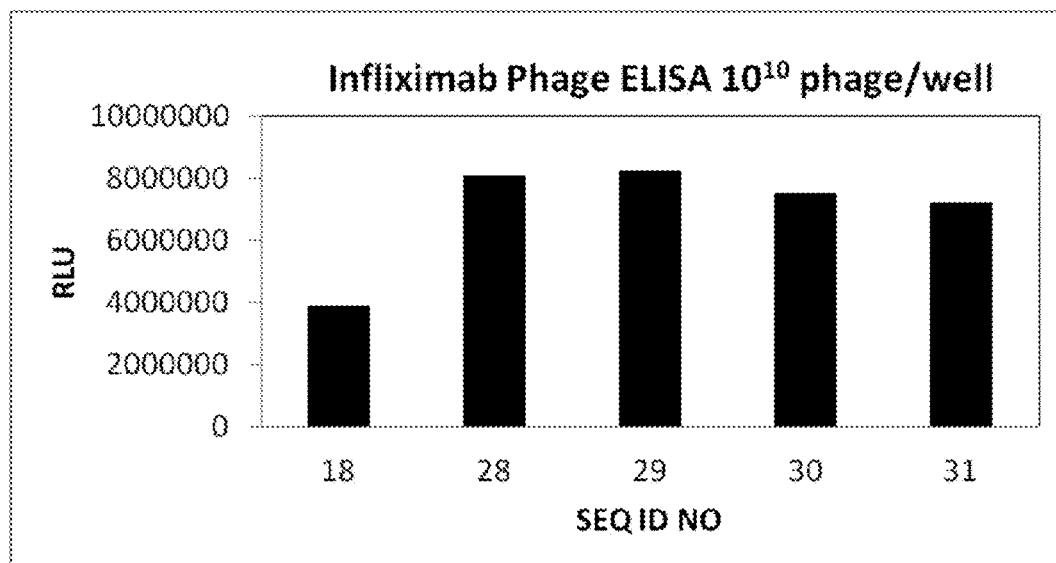
FIG. 9. Mutant phage ELISA showing linear fragments of SEQ ID NO: 18 that bind to infliximab.

Data in FIG. 8A shows the affinity biomatrix controlled release device loaded with 50 micrograms of infliximab has a cumulative release of infliximab of approximately 40% (SEQ ID NO: 24) and 55% (SEQ ID NO: 25) by weight at the 28 day time point whereas the unmodified control collagen sponge releases approximately 100% by weight. Data in FIG. 8B shows the affinity biomatrix controlled release device loaded with 200 micrograms of infliximab has a cumulative release of infliximab of approximately 89% (SEQ ID NO: 24) and 80% (SEQ ID NO: 25) by weight at the 28 day time point whereas the unmodified control collagen sponge releases approximately 100% by weight. The initial burst release of infliximab from the affinity peptide biomatrix controlled release device is significantly reduced as compared to the unmodified control collagen sponge.

Example 12

Mutant Phage ELISA

Site-directed mutagenesis was performed on affinity peptide SEQ ID NO: 18 to obtain a linear version of the peptide and to understand which amino acids are important for binding to infliximab. Mutants of the abovementioned affinity peptide were constructed by randomizing residues 3 through 6 and residues 15 through 18 of the wild type affinity peptide SEQ ID NO: 18, AG-XXXX-PWPPTAES-XXXX, where X denotes any of the 20 natural amino acids.

The respective custom oligonucleotide was obtained from Integrated DNA Technologies, Inc. (Coralville, Iowa). The oligonucletides were inserted into the pIX gene using standard protocols. First, the oligonucletides were phosphorylated using T4 polynucleotide kinase. Next, the phosphorylated oligonucletides were annealed to the ssDNA template. Using the Kunkel method, the annealed DNA was ligated using T4 DNA ligase and T7 DNA polymerase. The resultant DNA was isolated using isopropanol precipitation and a gel was run to confirm the reaction. Lastly, electro-competent *E. coli* cells were transformed with the purified DNA, plated out onto 2xYT/Tet/Xgal agar plates and were allowed to grow overnight to isolate single colonies. An aliquot of the transformed cells was allowed to grow overnight at 37° C. while shaking in 50 mL 2xYT/tet media. The phage was PEG precipitated following the procedure in Example 1. A phage titration was performed to determine the concentration of phage for the ELISA assay as described in Example 2. ELISA assays were performed following the procedure in Example 3 to identify fragments of SEQ ID NO: 18 that bind to infliximab. Data in FIG. 9 show the mutant affinity peptides, whose sequences are listed in FIG. 10, are binding to infliximab.

We claim:

1. A controlled release device comprising an affinity biomatrix, further comprising a polymer, infliximab and an affinity peptide toward infliximab having a peptide sequence selected from the group consisting of an affinity peptide toward infliximab having a peptide sequence selected from the group consisting of SEQ ID NO: 3 and SEQ ID NO: 13.

2. The controlled release device of claim 1, wherein the polymer is a natural polymer.

3. The controlled release device of claim 2, wherein the natural polymer is selected from the group consisting of collagen, elastin, keratin, silk, polysaccharides, GAGs, and combinations thereof.

4. The controlled release device of claim 3 wherein the polysaccharide is selected from the group consisting of starch, pectin, cellulose, alkyl cellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, cross-linked alginate/alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid, and polyglucuronic acid.

5. The controlled release device of claim 2, wherein the natural polymer is collagen.

6. The controlled release device of claim 2, wherein the natural polymer is decellularized tissue selected from the group consisting of skin, periosteum, perichondrium, synovium, fascia, mesenter, bone and sinew.

7. The controlled release device of claim 5, wherein the collagen is in the form of sponges, particles, injectable gels, injectable liquids, membranes, films, fibers and fiber based scaffolds.

8. A kit comprising an affinity biomatrix, further comprising a polymer and an affinity peptide toward infliximab having a peptide sequence selected from the group consisting of SEQ ID NO: 3 and SEQ ID NO: 13, and infliximab.

* * * * *

SEQUENCE LISTING

```
<160> NUMBER OF SEQ ID NOS: 32

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Gly Trp Thr Val Ala Tyr Val Pro Pro Gly Pro Ser Tyr Ala Thr
1               5                   10                  15

Ser

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Gly Tyr Val Cys Asp Pro Ala Gly Pro Asn Cys Trp Ala
1               5                   10

<210> SEQ ID NO 3
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 3

Ala Gly Thr Tyr Cys His Pro Asp Gln Leu Arg Asn Leu Cys Pro Val
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Gly Val Thr Cys Arg Met Thr Glu Tyr Gly Pro Met Cys Pro Thr
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Gly Asn Arg Cys Ala Tyr Ala Ala Gly Thr Ile Gln Cys Phe Pro
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Gly Glu Ile Cys Tyr Trp His Asp Thr Asp Trp Val Cys Thr Glu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Gly Thr His Cys Ser Tyr Val Leu Gly Arg Ile Glu Cys Leu Pro
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Gly Asn Tyr Cys His Pro Asp Gln Leu Ser Gln Phe Cys Ala Arg
1               5                   10                  15
```

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Gly Val Ala Cys His Ser Thr Gly Thr Asn Ile Tyr Thr Cys Thr
1               5                   10                  15

Tyr

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Gly Val Trp Cys Gly Asp Glu Thr Leu Pro Pro Ser Ile Cys Phe
1               5                   10                  15

Arg

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Gly Ser Leu Cys His Thr Val Gly Ser Gly Ile Tyr Asn Cys Thr
1               5                   10                  15

Lys

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Gly Ile Gln Cys His Asp Val Gly Ala Gly Val Val Thr Cys Thr
1               5                   10                  15

Tyr

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Gly Pro Pro Cys Ile Val Thr Gln Leu Ser Asp Leu Ser Phe Cys
1               5                   10                  15

Ala Pro

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Gly Ala Arg Cys Ala Pro Ala Phe Asp Ala Asn Trp Leu Ile Cys
1               5                   10                  15

Ser Asn

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Gly Pro Pro Cys Ala Ala Ala Met Ala Gln Ala Gln Leu Ala Cys
1               5                   10                  15

Thr His

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Gly Val Val Cys Ala Thr Pro Glu Trp Thr Trp Asp Pro Ala Cys
1               5                   10                  15

Ala Thr

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Gly Leu Leu Cys Ala Pro Ser Leu Asp Pro Asp Tyr Ile Leu Cys
1               5                   10                  15

Asp Gln

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Gly Leu Leu Cys Glu Pro Trp Pro Pro Thr Ala Glu Ser Ile Cys
1               5                   10                  15

Arg Ser

```
<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Gly Pro Pro Tyr Thr Val Phe Val His Leu
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Gly Tyr Cys Ile Ser Asp Tyr Ile Asp Pro Cys His
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Gly Pro Cys Ile Ser Asp Tyr Phe Asp Pro Cys His
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Gly Leu Cys Pro Glu Leu Pro His Cys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Gly Pro Cys Pro Glu Leu Pro His Cys Thr Tyr
1               5                   10

<210> SEQ ID NO 24
<211> LENGTH: 24
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (24)..(24)
<223> OTHER INFORMATION: Lys-(Propargylacetyl)
<220> FEATURE:
<223> OTHER INFORMATION: C-term amidated

<400> SEQUENCE: 24

Ala Gly Tyr Val Cys Asp Pro Ala Gly Pro Asn Cys Trp Ala Ser Gly
1               5                   10                  15

Gly Ser Gly Gly Ser Gly Gly Lys
            20

<210> SEQ ID NO 25
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (27)..(27)
<223> OTHER INFORMATION: Lys-(Propargylacetyl)
<220> FEATURE:
<223> OTHER INFORMATION: C-term amidated

<400> SEQUENCE: 25

Ala Gly Val Trp Cys Gly Asp Glu Thr Leu Pro Pro Ser Ile Cys Phe
1               5                   10                  15

Arg Ser Gly Gly Ser Gly Gly Ser Gly Gly Lys
            20                  25

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 26

Ala Gly Tyr Val Cys Asp Pro Ala Gly Pro Asn Cys Trp Ala Ser Gly
1               5                   10                  15

Gly Ser Gly Gly Ser Gly Gly Lys
            20

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 27

```
Ala Gly Val Trp Cys Gly Asp Glu Thr Leu Pro Pro Ser Ile Cys Phe
1               5                   10                  15

Arg Ser Gly Gly Ser Gly Gly Ser Gly Gly Lys
            20                  25
```

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Ala Gly Leu Tyr Val Ser Pro Trp Pro Pro Thr Ala Glu Ser Thr Ala
1               5                   10                  15

Ile Ile
```

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Ala Gly Leu Tyr Val Ser Pro Trp Pro Pro Thr Ala Glu Ser Thr Ala
1               5                   10                  15

Val Leu
```

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Ala Gly Leu His Val Tyr Pro Trp Pro Pro Thr Ala Glu Ser Thr Ala
1               5                   10                  15

Tyr Leu
```

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Ala Gly Ala Tyr Val Phe Pro Trp Pro Pro Thr Ala Glu Ser Thr Val
1               5                   10                  15

Thr Leu
```

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (15)..(18)
<223> OTHER INFORMATION: Any amino acid

<400> SEQUENCE: 32

Ala Gly Xaa Xaa Xaa Xaa Pro Trp Pro Pro Thr Ala Glu Ser Xaa Xaa
1               5                   10                  15

Xaa Xaa
```